United States Patent
Fürstner et al.

(10) Patent No.: US 9,802,965 B2
(45) Date of Patent: Oct. 31, 2017

(54) PROCESS FOR THE TRANS-SELECTIVE HYDROBORATION OF INTERNAL ALKYNES

(71) Applicant: STUDIENGESELLSCHAFT KOHLE MBH, Mülheim an der Ruhr (DE)

(72) Inventors: Alois Fürstner, Mülheim an der Ruhr (DE); Basker Sundararaju, Uttar Pradesh (IN)

(73) Assignee: STUDIENGESELLSCHAFT KOHLE MBH, Mülheim an der Ruhr (DE)

( * ) Notice: Subject to any disclaimer, the term of this patent is extended or adjusted under 35 U.S.C. 154(b) by 27 days.

(21) Appl. No.: 15/026,374

(22) PCT Filed: Sep. 30, 2014

(86) PCT No.: PCT/EP2014/070993
§ 371 (c)(1),
(2) Date: Mar. 31, 2016

(87) PCT Pub. No.: WO2015/049257
PCT Pub. Date: Apr. 9, 2015

(65) Prior Publication Data
US 2016/0244466 A1    Aug. 25, 2016

(30) Foreign Application Priority Data

Oct. 1, 2013    (EP) .................... 13186892

(51) Int. Cl.
*C07F 5/02*     (2006.01)
*B01J 31/22*    (2006.01)
*C07B 59/00*    (2006.01)

(52) U.S. Cl.
CPC .......... *C07F 5/025* (2013.01); *B01J 31/2295* (2013.01); *C07B 59/004* (2013.01); *C07F 5/02* (2013.01); *B01J 2231/323* (2013.01); *B01J 2531/821* (2013.01); *C07B 2200/09* (2013.01); *C07B 2200/13* (2013.01)

(58) Field of Classification Search
CPC .......... C07F 5/02; C07F 5/025; B01J 31/2295
See application file for complete search history.

(56) References Cited

U.S. PATENT DOCUMENTS

| 4,731,463 A | 3/1988 | Noth et al. |
| 2006/0142503 A1 | 6/2006 | Lang et al. |
| 2012/0220794 A1 | 8/2012 | Gazic Smilovic et al. |
| 2012/0231993 A1 | 9/2012 | Gazic Smilovic et al. |

FOREIGN PATENT DOCUMENTS

WO    2010 146172 A2    12/2010

OTHER PUBLICATIONS

Koren-Selfridge et al. "A Boron-Substituted Analogue of the Shvo Hydrogenation Catalyst: Catalytic Hydroboration of Aldehydes, Imines, and Ketones" Organometallics, 2009, vol. 28, pp. 2085-2090.*
Yan, et al., "Reactions of nido-1,2-(Cp*RuH)2B3H7 with RC.tplbond.CR' (R,R'=Ph; Me, Me) to yield novel metallacarboranes"; Journal of Organometallic Chemistry, 680 (1-2), pp. 66-80, (2003).
Koren-Selfridge, et al., "A Boron-Substituted Analogue of the Shvo Hydrogenation Catalyst: Catalytic Hydroboration of Aldehydes, Imines, and Ketones", Organometallics, 28, pp. 2085-2090, (2009).

* cited by examiner

*Primary Examiner* — Joseph Kosack
(74) *Attorney, Agent, or Firm* — Norris McLaughlin & Marcus, P.A.

(57) ABSTRACT

The present invention refers to a process for the trans-selective hydroboration of internal alkynes and the so-obtained products. The inventive process makes use of a borane of the formula $X^1X^2BH$ selected from the group of dialkyl boranes or di(alkoxy)boranes which are reacted with the internal alkynes in the presence of a cyclyopentadienyl-coordinated ruthenium catalyst.

11 Claims, 4 Drawing Sheets

PROCESS FOR THE TRANS-SELECTIVE HYDROBORATION OF INTERNAL ALKYNES

This application is a 371 of PCT/EP2014/070993, filed Sep. 30, 2014, which claims foreign priority benefit under 35 U.S.C. §119 of European Patent Application No. 13186892.9 filed Oct. 1, 2013, the disclosures of which are incorporated herein by reference.

The present invention refers to a process for the trans-selective hydroboration of internal alkynes and the so-obtained products.

The discovery of the hydroboration of olefins and alkynes heralded a new era of synthetic chemistry with profound implications for industrial practice (Brown, H. C. Hydroboration. W. A. Benjamin, Inc., New York, 1962; Pelter, A., Smith, K. & Brown, H. C. Borane Reagents. Academic Press, London 1988). The resulting organoborane derivatives are rather stable and hence much easier to handle than many of the traditional organometallic reagents; yet, they are readily engaged in an overwhelming number of synthetically useful transformations that give access to unparalleled structural and functional diversity as mandated by advanced organic synthesis and material science (Matteson, D. S. Stereodirected synthesis with organoboranes. Springer, Berlin, 1995). The reigning stereochemical paradigm of hydroboration is the suprafacial delivery of hydrogen and boron to the same π-face of a given starting material (cis-addition mode).

Figure 1:
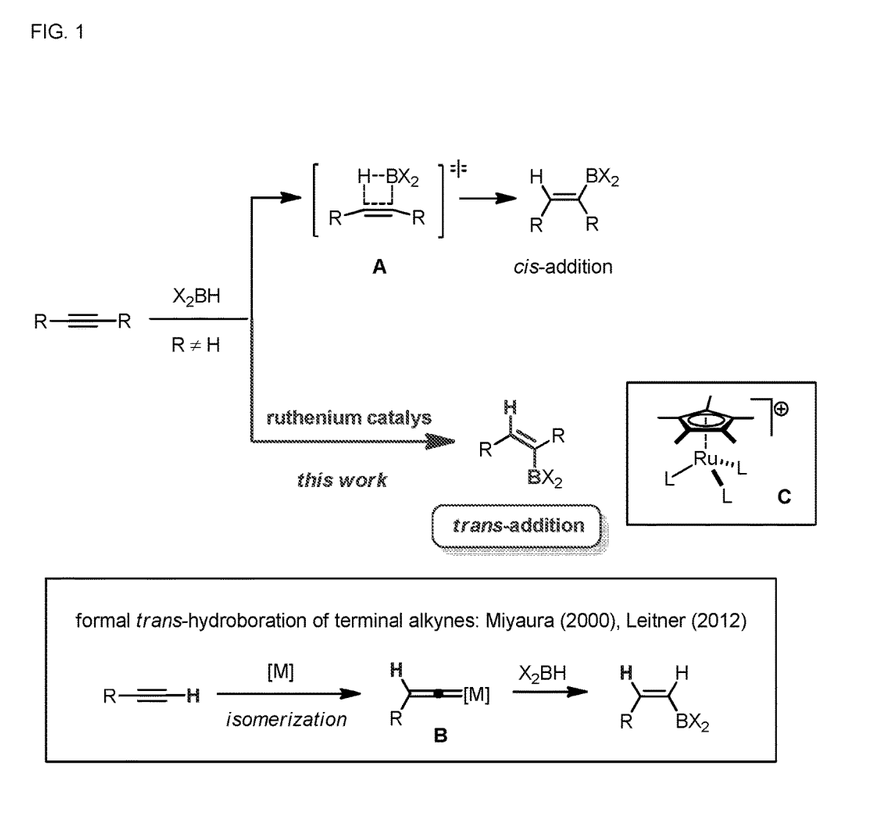

The hydroboration of alkynes is an indispensable method for the synthesis of alkenylboron reagents that find extensive use in preparative chemistry, most notably as nucleophiles in various types of transition metal catalyzed C—C-bond forming reactions (Hall, D. G. (Ed.), Boronic acids. Preparation, applications in organic synthesis and medicine. Wiley-VCH, 2005). The Suzuki cross coupling reaction is arguably the most important application of organoboron reagents in general and alkenylboron reagents in particular (Suzuki, A., Angew. Chem. Int. Ed. 50, 6723-6737 (2011)). Hydroboration proceeds concertedly via a four-center transition state A that delivers the hydrogen and the boron residue to the same π-face of the substrate as shown in FIG. 1 at the top. This stereochemical course is under stringent frontier-orbital control and converts internal alkynes—with high fidelity—into Z-configured alkenylboron derivatives, independent of the chosen borane reagent (Brown, H. C. Hydroboration. W. A. Benjamin, Inc., New York, 1962).

The syn-additon mode is also strictly obeyed when transition metals are used to catalyze such hydroboration reactions (Beletskaya, I. et al., Tetrahedron 53, 4957-5026 (1997)). In fact, only very few exceptions are documented where this rule is formally violated. Thus, terminal alkynes were shown to lead to a net anti-addition when reacted with catecholborane (cat-H) or pinacolborane (pin-H) in the presence of certain rhodium, iridium or ruthenium complexes as the catalysts (FIG. 1, bottom) (Ohmura, T. et al. J. Am. Chem. Soc. 122, 4990-4991 (2000); Gunanathan, C. et al. J. Am. Chem. Soc. 134, 14349-14352 (2012)). This unusual outcome, however, actually results from an initial rearrangement with formation of metal vinylidene complexes B as reactive intermediates. As a consequence, it is the alkyne proton itself—rather than the hydrogen from the borane reagent—that ends up anti to the boron moiety in the product, as unequivocally shown by labeling studies. For this very reason, this method does not work with internal alkynes, for which trans-hydroborations remain basically unknown. The only recorded exception is an indirect method employing the diboron reagent (pin)B—B(pin) (pin=4,4,5,5-tetramethyl-[1,3,2]dioxaborolanyl) in combination with NaOtBu, CuCl and a phosphine ligand in MeOH (Kim, H. R. et al., Chem. Commun. 47, 2943-2945 (2011)). When applied to bulky alkynes of the type ArC≡CtBu (Ar=aryl), the corresponding E-configured alkenylboronates are formed; upon the smallest decrease in size, however, the system relaxes and returns to the usual syn-addition pathway. First attempts to extend this chemistry to hydroboration, however, were largely unsuccessful.

In the state of art, some very specific hydroboration processes only have been made subject matter of patent applications in the last years. For example, U.S. Pat. No. 4,731,463 refers to a process for hydroboronizing alkenes or alkynes with catecholborane (1,3,2-benzodioxaborolane) optionally in the presence of an added organic solvent the reaction which is catalyzed by a complex compound having one of the formulas: (I) RhCl(CO)x[E(C6H5)3]3-x' wherein "E" is arsenic or phosphorous and "x" equals 0 or 1, (II) [RhCl(alkene)2]2' (III) [(C6H5)3P]3 3Ru(CO)ClH or (IV) [(C6H5)3P]3RuCl2, particularly suitable catalysts are, e.g. tris (triphenylphosphine)rhodium(I) chloride and bis(cyclooctadiene)rhodium(I) chloride.

Furthermore, US2006142503 describes a process for functionalizing isobutene polymers having terminal olefinic unsaturation by treating with the reaction product of a borane source with from 0.5 to 1.8 equivalents of an alkene having a molecular weight of less than 250 per mole of borane or by treating the isobutene polymer with the borane source in the presence of the alkene.

The inventors of the present invention found the first broadly applicable, functional group tolerant and highly stereoselective trans-hydroboration of internal alkynes. Therefore, the present invention is directed to a process for highly stereoselective trans-hydroboration of internal alkynes comprising the steps of reacting an alkyne of the formula I (I)

with a borane of the formula $X^1X^2BH$ in the presence of a ruthenium catalyst to yield an alkene of the general formula (II):

(II)

In the alkyne of the general formula (I) and in the alkene of the general formula (II), respectively,
$R^1$ and $R^2$ may be the same or different and may each be selected from:

a. straight chain or branched chain aliphatic hydrocarbons, preferably having 1 to 20 carbon atoms, or cyclic aliphatic hydrocarbons, preferably having 3 to 20 carbon atoms, said aliphatic hydrocarbons optionally including heteroatoms and/or aromatic hydrocarbons and/or heteroaromatic hydrocarbons in the chain and/or having one or more substituents selected from $C_1$-$C_{20}$-alkyl, $C_5$-$C_8$-heterocycloalkyl or $C_6$ to $C_{20}$ aromatic hydrocarbon, $C_5$ to $C_{20}$ heteroaromatic hydrocarbon or aryl-$(C_1$-$C_6)$-alkyl, heteroaryl-$(C_1$-$C_6)$-alkyl, or heteroatoms, or b. aromatic hydrocarbons having 5 to 20 carbon atoms or heteroaromatic hydrocarbons having 1 to 20 carbon atoms, said aromatic or heteroaromatic hydrocarbons each optionally having one or more substituents selected from $C_1$-$C_{20}$-alkyl, $C_5$-$C_8$-heterocycloalkyl or $C_6$ to $C_{20}$ aromatic hydrocarbon, $C_5$ to $C_{20}$ heteroaromatic hydrocarbon or aryl-$(C_1$-$C_6)$-alkyl, heteroaryl-$(C_1$-$C_6)$-alkyl, heteroatoms, or $R^1$ and $R^2$ together form an aliphatic hydrocarbon chain having 4 to 30 carbon atoms, optionally including heteroatoms and/or aromatic hydrocarbons in the chain and/or optionally having one or more substituents selected from $C_1$-$C_{20}$-alkyl, $C_5$-$C_8$-heterocycloalkyl or $C_6$ to $C_{20}$ aromatic hydrocarbon, $C_5$ to $C_{20}$ heteroaromatic hydrocarbon or aryl-$(C_1$-$C_6)$-alkyl, heteroaryl-$(C_1$-$C_6)$-alkyl, said aliphatic hydrocarbon chain optionally being substituted by one or more substituents selected from heterosubstituents, straight chain, branched chain, cyclic aliphatic $C_1$ to $C_{20}$ hydrocarbons, $C_6$ to $C_{20}$ aromatic hydrocarbon, $C_5$ to $C_{20}$ heteroaromatic hydrocarbon, aryl-$(C_1$-$C_6)$-alkyl, or heteroaryl-$(C_1$-$C_6)$-alkyl or heteroatoms.

Preferably, $R^1$ and $R^2$ may be the same or different and may each be selected from straight chain or branched chain aliphatic hydrocarbons having 1 to 20 carbon atoms optionally including heteroatoms and/or aromatic hydrocarbons in the chain or aromatic hydrocarbons having 5 to 20 carbon atoms, optionally having one or more substituents selected from $C_1$-$C_{20}$-alkyl, $C_5$-$C_8$-heterocycloalkyl or $C_6$ to $C_{20}$ aromatic hydrocarbon, $C_5$ to $C_{20}$ heteroaromatic hydrocarbon or aryl-$(C_1$-$C_6)$-alkyl, heteroaryl-$(C_1$-$C_6)$-alkyl, or heteroatoms, or $R^1$ and $R^2$ together form an aliphatic hydrocarbon chain structure having 8 to 20 carbon atoms, optionally including heteroatoms and/or aromatic hydrocarbons in the chain and/or optionally having one or more substituents selected from $C_1$-$C_{20}$-alkyl, $C_5$-$C_8$-heterocycloalkyl or $C_6$ to $C_{20}$ aromatic hydrocarbon, $C_5$ to $C_{20}$ heteroaromatic hydrocarbon or aryl-$(C_1$-$C_6)$-alkyl, heteroaryl-$(C_1$-$C_6)$-alkyl, said chain structure optionally being substituted by one or more substituents selected from heterosubstituents, straight chain, branched chain, cyclic aliphatic $C_1$ to $C_{20}$ hydrocarbons, $C_6$ to $C_{20}$ aromatic hydrocarbon, $C_5$ to $C_{20}$ heteroaromatic hydrocarbon, aryl-$(C_1$-$C_6)$-alkyl, or heteroaryl-$(C_1$-$C_6)$-alkyl.

$R^1$ and $R^2$ should preferably have a lower affinity to the Ru-central atom in the ruthenium complex than the alkynyl moiety in order to avoid blocking of the reactive site thereof.

The borane of the formula $X^1X^2BH$ is selected from the group of dialkyl boranes or di(alkoxy)boranes wherein $X^1$ and $X^2$ may be the same or different and may each be selected from straight chain, branched chain or cyclic aliphatic hydrocarbons, preferably having 1 to 20, preferably 1 to 16 carbon atoms, or $X^1$ and $X^2$ together form an aliphatic hydrocarbon chain having 2 to 20 carbon atoms, preferably 2 to 10 carbon atoms in the chain, said aliphatic hydrocarbon group or chain optionally bound to the boron via an —O-bridge and optionally including heteroatoms in the chain and/or optionally having one or more substituents selected from $C_1$-$C_{20}$-alkyl, $C_5$-$C_8$-heterocycloalkyl or $C_6$ to $C_{20}$ aromatic hydrocarbon, $C_1$ to $C_{20}$ heteroaromatic hydrocarbon or aryl-$(C_1$-$C_6)$-alkyl, heteroaryl-$(C_1$-$C_6)$-alkyl, having identical or different alkyl groups with 2 to 12 carbon atoms or heteroatoms.

Preferably, $X^1$ and $X^2$ are each bound to the boron atom via an —O-bridge and form—together with the —O-bridges—a hydrocarbon ring having 2 to 12 carbon atoms, said hydrocarbon ring optionally being substituted by one or more substituents selected from heterosubstituents, $C_1$ to $C_6$ straight chain, branched chain or cyclic aliphatic hydrocarbons, said hydrocarbon heterocyclic ring structure having 2 to 12 carbon atoms being represented by the general formula:

More preferably, the borane of the formula $X^1X^2BH$ is represented by the formula in which X1 and X2 form a $C_1$ to $C_6$-hydrocarbon chain being bound to the boron atom via-O-bridges and being substituted by hydrogen, methyl, ethyl, propyl, butyl or isomers thereof. A simple example is pin-H as represented by the following formula:

pin-H or its analogues having 3 or 4 carbon atoms in the chain and being substituted by hydrogen or lower alkyl.

The catalyst used in the inventive process is a cyclopentadienyl-coordinated ruthenium complex containing the following substructure:

wherein $R_{cp1}$ to $R_{cp5}$ may be the same or different and may each be selected from hydrogen or from straight chain, branched chain or cyclic aliphatic hydrocarbons, preferably having 1 to 20 carbon atoms, optionally including heteroatoms and/or aromatic hydrocarbons in the chain and/or optionally having one or more substituents selected from $C_1$-$C_{20}$-alkyl, heterocycloalkyl, $C_5$ to $C_{20}$ aromatic hydrocarbon, $C_5$ to $C_{20}$ heteroaromatic hydrocarbon or aryl-$(C_1$-$C_6)$-alkyl, heteroaryl-$(C_1$-$C_6)$-alkyl or heteroatoms and wherein further ligands are coordinated to the central atom Ruthenium. Said ligands L are generally known in the state of art and serve for stabilizing the Ru-complex by sharing electrons with the Ru orbitals. Thus, they can be selected from electron-donating ligands/substituents, for example such as hydrogen, halogen, $CH_3CN$, cycloalkyldiene having 8 to 12 carbon atoms, Preferred catalysts are $[Cp^*RuL_3]X$ wherein $Cp^*=\eta^5$-$C_5R_{5cp}$ with each $R_{cp}$ being H or preferably $CH_3$, and L being the same or different ligand/substituent and being selected from electron-donating ligands/substituents such as hydrogen, halogen, $CH_3CN$, cycloalkyldiene having 8 to 12 carbon atoms, or a dimer of the formula $[Cp^*RuH_2]_2$ wherein Cp*=$\eta^5$-C$_5$R$_5$ with R being H or CH$_3$. The Ru-complex is preferably a cationic complex with an anionic counter ion X that is weakly coordinating, such as PF$_6^-$, SbF$_6^-$, BF$_4^-$, ClO$_4^-$, F$_3$CCOO$^-$, Tf$_2$N$^-$, (Tf=trifluoromethanesulfonyl), TfO$^-$, tosyl, [B[3,5-(CF$_3$)$_2$ C$_6$H$_3$]$_4$]$^-$, B(C$_6$F$_5$)$_4^-$), Al(OC(CF$_3$)$_3$)$_4^-$.

The solvent used in the inventive process should be a low donor solvent and may be selected from aliphatic, cycloaliphatic solvents, esters, ethers, ketones or mixtures thereof which may be substituted by one or more heteroatoms such as hexane, CHCl$_3$, CH$_2$Cl$_2$, CH$_3$CN, ethyl acetate, acetone, THF, diethyl ether or methyl tert-butyl ether, as long as they are not detrimental to the catalysed reaction. If the alkyne of the formula (I) itself is a liquid or in a liquid state, there might be no need for a separate solvent. The catalyst is generally used in a molar ratio of 0.1 to 10 mol-%, preferably 1 to 5 mol-% referred to the alkyne of the general formula (I).

The inventive process can be carried out in a temperature range from −20° C. to 100° C., preferably at ambient temperature of between 0° and 30° C., and it proceeds at normal pressure already. If needed, the reaction can be carried out in a protective atmosphere such as argon.

A heterosubstituent as defined according to the invention can be selected from —O—, =O, F, Cl, Br, I, CN, NO$_2$, a monohalogenomethyl group, a dihalogenomethyl group, a trihalogenomethyl group, CF(CF$_3$)$_2$, SF$_5$, amine bound through N atom, —O-alkyl (alkoxy), —O-aryl, —O—SiR$^S_3$, S—R$^S$, S(O)$_2$—R$^S$, S(O)$_2$—R$^S$, CO$_2$—R$^S$, amide, bound through C or N atom, formyl group, C(O)—R$^S$. R$^S_3$ may be, independently from each other, the same or different and may be each an aliphatic, heteroaliphatic, aromatic or heteroaromatic group, each optionally being further substituted by one or more heterosubstituents, aliphatic, heteroaliphatic, aromatic or heteroaromatic groups. Preferably, the heterosubstituent is selected from =O, F, Cl, Br, I, CN, NO$_2$, a monohalogenomethyl group, a dihalogenomethyl group, a trihalogenomethyl group, CF(CF$_3$)$_2$, SF$_5$, amine bound through N atom, —O-alkyl (alkoxy), —O-aryl.

In more detail, C$_1$-C$_{20}$-alkyl can be straight chain or branched and has 1, 2, 3, 4, 5, 6, 7, 8, 9, 10, 11, 12, 13, 14, 15, 16, 17, 18, 19 or 20 carbon atoms. Alkyl might be lower alkyl such as C$_1$-C$_5$-alkyl, in particular methyl, ethyl, propyl, isopropyl, butyl, isobutyl, sec-butyl or tert-butyl, likewise pentyl, 1-, 2- or 3-methylpropyl, 1,1-, 1,2- or 2,2-dimethylpropyl, 1-ethylpropyl, hexyl, 1-, 2,3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl. Substituted alkyl groups are trifluoromethyl, pentafluoroethyl and 1,1,1-trifluoroethyl.

Cycloalkyl might preferably be C$_3$-C$_{10}$-alkyl and may be cyclopropyl, cyclobutyl, cyclopentyl, cyclohexyl or cycloheptyl.

Alkenyl might be C$_2$-C$_{20}$ alkenyl. Alkynyl might be C$_2$-C$_{20}$ alkynyl.

Halogen is F, Cl, Br or I.

Alkoxy is preferably C$_2$-C$_{10}$ alkoxy such as methoxy, ethoxy, propoxy, iso-propoxy, tert-butoxy etc.

Heterocycloalkyl having one or more heteroatoms selected from among N, O and S is preferably 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl.

Optionally substituted means unsubstituted or monosubstituted, disubstituted, trisubstituted, tetrasubstituted, pentasubstituted, or even further substituted for each hydrogen on the hydrocarbon.

Aryl might be phenyl, naphthyl, biphenyl, anthracenyl, and other polycondensed aromatic systems.

Aryl-(C$_1$-C$_6$)-alkyl might be benzyl or substituted benzyl.

Heteroaryl having one or more heteroatoms selected from among N, O and S is preferably 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, also preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-Indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, also preferably 1,3-benzodioxol-5-yl, 1,4-benzodioxan-6-yl, 2,1,3-benzothiadiazol-4- or -5-yl or 2,1,3-benzoxadiazol-5-yl.

The invention is further illustrated by the attached drawings, wherein:

FIG. 1 illustrates the conventional hydroboration of alkynes (top) occurring via a four-center transition state A under frontier orbital control. In the essence, the HOMO of the alkyne donates electron density into a empty boron-centered π-orbital, while electron density is simultaneously back-donated from the bonding B—H σ-orbital into the LUMO of the alkyne. As a consequence of this concerted process, hydrogen and boron are added in a cis-fashion to the triple bond. The trans-addition mode engendered by cationic ruthenium complexes of type C described herein (center) stands in marked contrast to this established stereochemical pattern. The only other widely applicable formal trans-hydroboration known in the literature (bottom) is limited to terminal alkynes. However, it is not a regular 1,2-addition process but proceeds via an initial isomerization with formation of a metal vinylidene intermediate (B). As a consequence, it is the H-atom of the alkyne itself rather than the H-atom of the reagent that ends up trans to the boron entity;

The inventors have carried out an initial screening of catalysts and boranes for the trans-hydroboration of internal alkynes. The results are indicated in the following Table 1.

to work up. Unless stated otherwise, the yields refer to analytically pure isolated material.

Thus, the reaction of cycloalkyne 1 with 9-H—BBN dimer in the presence of [Cp*Ru(MeCN)$_3$]PF$_6$ (3) (5 mol %) as precatalyst gave a product mixture (entry 1). The use of catecholborane (cat-H)—despite the excellent track record of this reagent in metal catalyzed hydroborations—resulted in low conversion (<20%, GC) and an isomer ratio (E:Z=1.2:1) (entry 2).

Although catecholborane and pinacolborane exhibit comparable reactivity in uncatalyzed hydroboration reactions, the inventors have found that they perform markedly different in the presence of [Cp*Ru(MeCN)$_3$]PF$_6$ (3). Thus, addition of 5 mol % of this complex to a solution of 1 and pin-H in CH$_2$Cl$_2$ resulted in a very fast (<10 min), clean and exquisitely trans-selective hydroboration (E:Z≥98:2, GC)

TABLE 1

Initial screening of catalysts and boranes for the trans-hydroboration of internal alkynes.

| Entry | Borane | [Ru] | E:Z | Yield (%) |
|---|---|---|---|---|
| 1 | 9-H-BBN | 3 | — | — [a] |
| 2 | cat-H | 3 | 1.2:1 | <20 (GC) [b] |
| 3 | pin-H | 4 | 75:25 | 84 |
| 4 | pin-H | 3 | ≥98:2 | 95 |
| 5 | pin-H | 3 | ≥98:2 | 88 [c] |
| 6 | pin-D [d] | 3 | ≥98:2 | 88 [d] |
| 7 | pin-H | 5 + AgOTf [e] | ≥98:2 | 71 |
| 8 | pin-H | 5 | ≥98:2 | 44 (GC) [b] |
| 9 | pin-H | 7 | ≥98:2 | 67 |
| 10 | pin-H | 6 | 95:5 | 15 (GC) [b] |
| 11 | pin-H | 8 | 98:2 | 24 (GC) [b] |

[a] mixture;
[b] conversion rather than isolated yield;
[c] the reaction was performed in the dark;
[d] the deuterium content in the reagent was ≈ 95%, in the product ≈ 93% (NMR);
[e] complex 5 was ionized on addition of AgOTf (5 mol %) prior to the addition of borane and substrate.

The reactions as indicated in Table 1 were carried out at 1 M concentration in CH$_2$Cl$_2$ under argon. The E:Z ratios were determined by GC and refer to the crude material prior (entry 4). On a 5 mmol scale, product E-2 was isolated in 91% yield using only 3 mol % of the ruthenium catalyst. When the loading was further reduced to 1 mol %, the reaction still proceeded smoothly, reaching ≥95% conversion within 3 h at ambient temperature. Importantly, GC-monitoring showed that the E/Z-ratio was consistently high throughout the entire course of the reaction. The same excellent E-selectivity was recorded when the hydroboration was performed in the dark, which excludes that the trans-alkenylborane product is formed by a secondary photochemical Z→E isomerization (entry 5). Likewise, authentic Z-2 remained unchanged when exposed to catalytic amounts of complex 3 in CH$_2$Cl$_2$. As an additional control experiment, deuterated pinacolborane (pin-D, ≈95% D) was used to rule out that the hydrogen atom residing trans to the boronate unit in the product derives from any other hydrogen source than the chosen borane reagent (≈93% deuterium incorporation, NMR) (entry 6). Collectively, these data suggest that the observed trans-addition is an inherent feature of the new methodology, and that the reaction is a true hydroboration rather than an isomerization process.

In analogy to pinacol borane, other heterocyclic borane reagents can also be used for the present trans-addition reaction. As a representative example, the following reaction scheme illustrates the use of 4,4,6-trimethyl-1,3,2-dioxaborinane Since all other metal-catalyzed hydroborations of internal alkynes follow the traditional syn-addition mode, utmost care was taken to confirm the unusual stereochemical outcome of the new procedure. The trans-configuration of product E-2 is evident from its spectroscopic data and was confirmed by comparison (GC, NMR) with an authentic sample of Z-2 made by conventional hydroboration of 1. Furthermore, single crystals suitable for X-ray diffraction analysis could be grown (see insert in Table 1); the structure of E-2 in the solid state unambiguously confirms the constitution and configuration of this product.

A brief survey showed that the use of [Cp*Ru(MeCN)$_3$] PF$_6$ (3) in CH$_2$Cl$_2$ is a preferred catalyst. Full conversion could also be reached in THF, whereas 1,4-dioxane as cosolvent caused a rate-deceleration and toluene basically halted the conversion (<10%, GC). This result is thought to reflect the affinity of [LRu(MeCN)$_3$]$^+$ (L=Cp, Cp*) towards arenes (and other conjugated π-systems), which leads to the formation of kinetically fairly stable adducts of type [Cp*Ru (ηq$^6$-arene)]$^+$. The inventors assume that a similar interaction explains why catecholborane with its electron rich arene ring is less effective than the purely aliphatic pinacolborane as the reagent in the present trans-addition, whereas these reagents show only gradually different reactivity vis-à-vis alkynes otherwise.

Formal replacement of the labile MeCN ligands on the cationic [Cp*Ru]$^+$ template by a kinetically more tightly bound cyclooctadiene (cod) moiety allows the reaction still to proceed but makes it somewhat less productive. Whereas the cationic species [Cp*Ru(cod)]OTf gave a respectable yield of 71% (Table 1, entry 7), the neutral variant [Cp*Ru (cod)Cl] (5) furnished no more than 44% conversion (GC) after 1 h (entry 8). In this case, the borane reagent itself may help release a cationic species in solution by slow abstraction of the chloride from the ruthenium precatalyst. A similar process might account for the activation of the chloride-bridged complex 7 (entry 9). Although the tested precatalysts greatly differ in efficiency, the E/Z-ratio was high in all cases, which may indicate the formation of a (largely) common active species. Moreover, it is unlikely that the actual catalyst is an ordinary ruthenium hydride, since complexes 6 and 8 comprising a preformed Ru—H bond gave rather poor results (entries 10, 11).

Of mechanistic significance is the observation of the inventors that the exquisite trans-selectivity is compromised upon formal replacement of the Cp* unit by the parent unsubstituted cyclopentadienyl (Cp) ring present in [CpRu (MeCN)$_3$]PF$_6$ (4), although the trans-addition product is still formed as the major compound (entry 3 versus entry 4). Since this structural change hardly affects the electronic properties of the ruthenium center, the stereo determining step of the catalytic cycle likely has a large steric component. A possible rationale is outlined below.

Next, the optimal reaction conditions were applied to a set of representative alkyne derivatives to explore the scope and limitations of the new procedure. As can be seen from the results compiled in FIG. 2, good to outstanding trans-selectivity was observed for a variety of substrates and the chemical yields were also good to excellent (panels A and B). In close analogy to the uncatalyzed hydroboration (Brown, H. C. Hydroboration. W. A. Benjamin, Inc., New York, 1962; Pelter, A., Smith, K. & Brown, H. C. Borane Reagents. Academic Press, London 1988), unsymmetrical alkynes lead to the formation of regioisomers, with a certain preference to place the boronate residue away from the bulkier substituent (panel B); careful NMR analysis confirmed that either regioisomer comprises an E-olefin subunit.

Most importantly, a variety of functional groups in the reaction system is tolerated, including ethers, esters, carbamates, acetals, nitriles, aryl and alkyl halides, and a primary alkyl tosylate. Even readily reducible sites such as a ketone, a nitro group, or the N—O bond of a Weinreb amide remained intact. Equally remarkable is the fact that an internal acetylene could be selectively hydroborated in the presence of a terminal olefin; the obvious "alkynophilicity" of the catalyst has mechanistic implications, too. Thus, the skilled man can easily test the matching conditions for the alkyne, ruthenium catalyst and borane.

Figure 2:
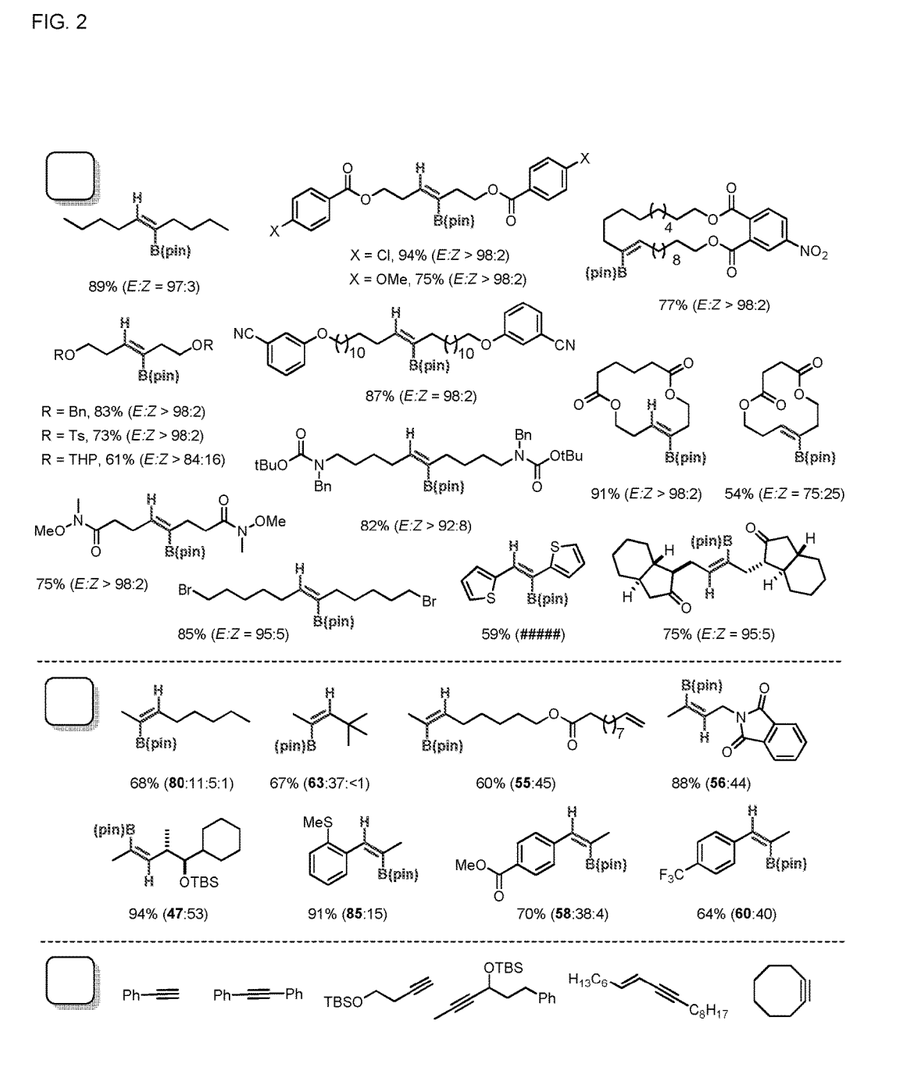
FIG. 2 gives an overview over the substrate scope, functional group tolerance and stereoselectivity of the ruthenium catalyzed trans-hydroboration. Unless stated otherwise, all reactions were performed at ambient temperature in CH$_2$Cl$_2$ (1 M) under argon using 5 mol % of [Cp*Ru(MeCN)$_3$]PF$_6$ as the catalyst; depending on the substrates, the reaction times varied between 30 min and 20 h, except for the thiophene derivative, which took 72 h to reach full conversion. Panel A: products derived from symmetrical alkynes; panel B: products derived from unsymmetrical alkynes; only one isomer is depicted (the data in brackets show the isomer ratio (GC) in the crude material, with the depicted isomer in bold); panel C: products with less reactivity in the inventive process.

The known affinity of [Cp*Ru] to arenes explains why tolane hardly reacts under the above conditions (panel C), but modifying the reactions conditions including testing different Ru-catalysts and boranes should enable the skilled man to find out suitable conditions. The inventors assume that electron withdrawing substituents on the aromatic ring might destabilize sandwich complexes of the general type [Cp*Ru(η$^6$-arene)]$^+$ (Gill, T. P. et al., *Organometallics* 1, 485-488 (1982); Schmid, A. et al., *Eur. J. Inorg. Chem.* 2255-2263 (2003)). In fact, arylalkynes bearing electron withdrawing groups (—CF$_3$, —COOMe) on the aromatic ring reacted well, although they took longer to reach full conversion. Particularly noteworthy in this context is the successful trans-hydroboration of sulfur-containing substrates. Though electron rich, the thiophilicity of ruthenium outweighs 7-complex formation and seems to direct the catalyst towards the triple bond. In any case, the compatibility of an unhindered thioether or a thiophene unit with a reaction catalyzed by a soft transition metal species is quite remarkable.

Despite this significant scope and functional group tolerance, a few limitations of the new trans-hydroboration reaction were noticed. Whereas the 14-membered cycloalkyne 1 reacted with exquisite E-selectivity (E:Z≥98:2), its 12-membered homologue gave an isomer mixture (E:Z=75:25, see panel A), and cyclooctyne was merely polymerized (panel C). This trend is ascribed to ring strain, which strongly disfavors E-configured cycloalkenes over the corresponding Z-isomers as the ring size decreases. Another limitation was encountered with terminal alkynes, which failed to react under standard conditions.

Although it is premature at this stage to draw a conclusive mechanistic picture, the basic features of the trans-selective hydroboration can be rationalized as follows. NMR inspection of a 1:1 mixture of pinacolborane and [Cp*Ru(MeCN)$_3$]PF$_6$ (3) in CD$_2$Cl$_2$ in the absence of an alkyne substrate showed no signs of chemical reaction or strong interaction of the partners; in any case, distinct metal boryl or metal hydride complexes could not be observed. This result is in line with the screening data that had shown the poor performance of preformed ruthenium hydride complexes in the present reaction. On the other hand, alkynes are known to readily engage with complexes of the general type [LRu]$^+$ (L=Cp, Cp*), leading to the coupling of two substrate molecules via ruthenacyclic intermediates (Trost, B. M. et al., *Angew. Chem. Int. Ed.* 44, 6630-6666 (2005)). This smooth C—C-bond formation is obviously outperformed by the trans-hydroboration presented herein.

Figure 3:
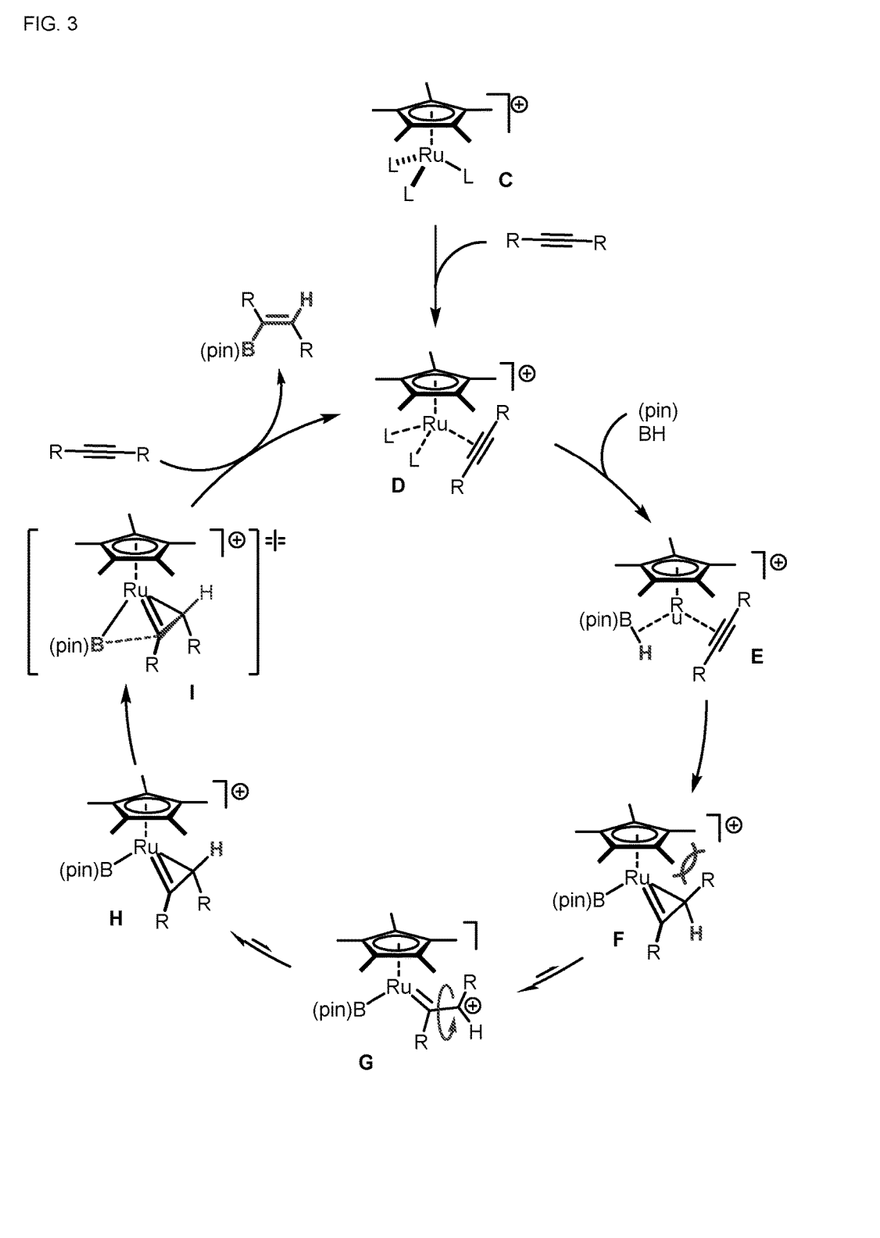
FIG. 3 illustrates a possible scenario as sketched by the inventors that explains the course of the trans-hydroboration reaction and encompasses the currently available mechanistic information; and, FIG. 4 illustrates the preparation of a di- and trisubstituted E-cycloalkene by derivatization of E-2 as explained below.

The inventors assume that binding of an alkyne to the electrophilic metal center of C subsequently favors coordination of the borane rather than of a second alkyne on electronic grounds (FIG. 3). In the resulting loaded complex E, the acetylene moiety is supposed to function as a four-electron donor, which explains why alkenes do not react under the chosen conditions. This bonding situation, in turn, facilitates an inner-sphere nucleophilic delivery of the hydride with formation of a metallacyclopropene F ($\eta^2$-vinyl complex) without prior generation of a discrete Ru—H species. It is very well precedented that the substituents at the β-carbon atom of such complexes are configurationally labile and can easily swap places via a $\eta^2 \rightarrow \eta^1 \rightarrow \eta^2$ hapticity change (Frohnapfel, D. S. et al., *Coord. Chem. Rev.* 206-207, 199-235 (2000)). As they are approximately orthogonal to the plane of the metallacyclopropene, the sheer size of the Cp* ring will exert a massive influence on the stereochemical outcome. As a consequence, isomer H, in which the hydrogen rather than the R group is oriented towards the bulky lid, will be largely favored over F. This decisive steric factor loses weight if the lateral methyl groups of the Cp* ring are formally removed and [CpRu]-based catalysts are used. The trajectory of the ensuing reductive elimination places the boron entity anti to the hydrogen atom and hence leads to the formation of an E-configured alkenylboronate product.

Figure 4:
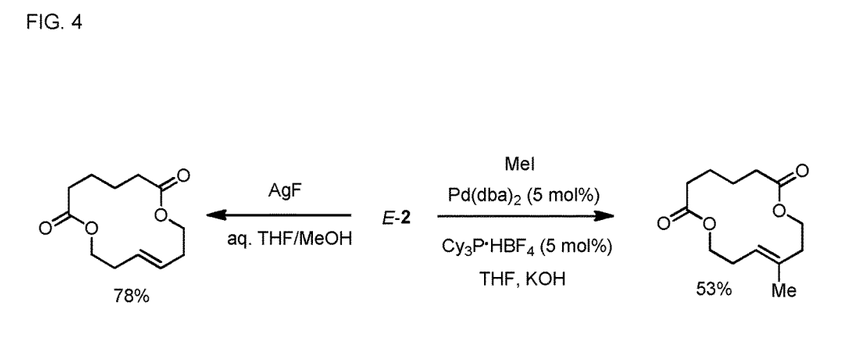

Of the countless possible derivatizations of the E-alkenyl-boronates made available by this convenient new procedure, the inventors explored the protodeborylation of E-2 with AgF in aqueous medium as well as an equally stereo-retentive Suzuki coupling with methyl iodide (FIG. 4). Both reactions led, without any detectable loss of stereochemical integrity, to E-configured cycloalkenes.

Thus, by the present invention, the inventors have shown that simple ruthenium catalysts, most notably the commercially available complex [Cp*Ru(MeCN)$_3$]PF$_6$ (Cp*=$\eta^5$-C$_5$Me$_5$), allow the fundamental and largely unchallenged rule of suprafacial delivery of hydrogen and boron to the same π-face of a given starting material (cis-additon mode) to be broken for internal alkynes as the substrates. The searching of libraries of matching candidates of alkyne, ruthenium catalyst and borane provides the simple means of finding the best system for a given transition Ru-catalyzed conversion. This procedure is simple and can be performed rapidly by standard laboratory techniques or, alternatively, with modern instruments which are customary in combinatorial catalysis. The resulting trans-selective hydroboration opens a practical new entry into E-configured alkenylboron derivatives which could previously only be made by indirect routes. The inventors expect this stereo-complementary methodology to add another dimension to the uniquely prolific field of organoboron chemistry. The inventive alkenylboron derivatives can be used for further synthesis of, for example, drug compounds or drug candidates, natural products, fine chemicals, agrochemicals, polymers, liquid crystals, fragrances, flavors, cosmetic ingredients, sun protective agents. Furthermore, they can be used for the preparation of compound libraries by combinatorial or parallel synthesis.

The invention is further illustrated by the general method for trans-hydroboration as shown in Example 1 and further exemplified in the subsequent Examples 2 to 26 for various products of the trans-hydroboration of internal alkynes.

EXAMPLE 1

(E)-11-(4,4,5,5-Tetramethyl-1,3,2-dioxaborolan-2-yl)-1,8-dioxacyclotetradec-11-ene-2,7-dione (E-2)

A flame-dried 10 mL Schlenk tube was charged under Ar with [Cp*Ru(CH$_3$CN)$_3$]PF$_6$ (75.6 mg, 0.15 mmol) and CH$_2$Cl$_2$ (5 mL) and the resulting solution was cooled to 0° C. with an ice bath. Pinacolborane (872 μL, 6 mmol) and alkyne 1 (1.12 g, 5 mmol) were successively added, the ice bath was removed and the solution stirred for 4 h at ambient temperature. For workup, the solvent was evaporated and the residue passed through a short column of silica, eluting with EtOAc/hexanes (1/4), to give alkenylboronate E-2 as a white crystalline solid (1.61 g, 91%, E/Z≥98:2). When the same reaction performed at 0.2 mmol scale, the product was isolated in 96% yield. Mp=66.7-70.4° C.; $^1$H NMR (CDCl$_3$, 400 MHz): δ 6.06 (1H, t, J=7.0 Hz), 4.18 (2H, t, J=5.5 Hz), 4.12 (2H, t, J=5.5 Hz), 2.71 (2H, dt, J=5.5, 7.1 Hz), 2.41 (2H, t, J=5.0 Hz), 2.34-2.24 (4H, m), 1.65-1.55 (4H, m), 1.22 (s, 12H); $^{13}$C NMR (CDCl$_3$, 125 MHz): δ 173.2, 173.1, 145.8, 83.0, 64.2, 63.2, 36.1, 34.9, 34.8, 30.0, 24.7, 24.5, 24.5 (the C-atom directly attached to boron is broadened and could not be precisely localized); $^{11}$B NMR (CDCl$_3$, 128 MHz): δ 30.6; IR (thin film): 2965, 1720, 1644, 1265, 1134, 861, 708 cm$^{-1}$, HRMS (ESI): m/z calcd for C$_{18}$H$_{29}$BO$_6$Na [M$^+$+Na]: 375.1947. found: 375.1949.

EXAMPLE 2

12-(H$^2$)-(E)-11-(4,4,5,5-Tetramethyl-1,3,2-dioxaborolan-2-yl)-1,8-dioxacyclotetradec-11-ene-2,7-dione [D]-E-2

White solid (62 mg, 88%); $^1$H NMR (CDCl$_3$, 400 MHz): δ 4.19 (2H, t, J=5.3 Hz), 4.13 (2H, t, J=5.5 Hz), 2.71 (2H, t, J=5.4 Hz), 2.42 (2H, t, J=5.3 Hz), 2.35-2.23 (4H, m), 1.66-1.54 (4H, m), 1.23 (12H, 5), $^{13}$C NMR (CDCl$_3$, 125 MHz): δ 173.0, 172.8, 145.2 (t, J=23.42 Hz), 82.7, 64.0, 63.0, 35.8, 34.6, 34.5, 29.6, 24.4, 24.3, 24.2 (the C-atom directly attached to boron is broadened and could not be precisely localized); $^2$H NMR (CH$_2$Cl$_2$, 92 MHz, 22° C.): δ 6.1, $^{11}$B NMR (CDCl$_3$, 128 MHz): δ 30.6; HRMS (ESI): m/z calcd for C$_{18}$H$_{28}$BO$_6$DNa [M$^+$+Na]: 376.2010. found: 376.2012.

EXAMPLE 3

(E)-2-(Dec-5-en-5-yl)-4,4,5,5-tetramethyl-1,3,2-dioxaborolane

Colorless oil (237 mg, 89%); reaction time=1 h; $^1$H NMR (CDCl$_3$, 300 MHz): δ=5.97 (1H, t, J=7.5 Hz), 2.29 (2H, q, J=7.1, 14.2 Hz), 2.07 (2H, t, J=6.9 Hz), 1.40-1.28 (m, 8H), 1.25 (12H, s), 0.93-0.81 (6H, m); $^{13}$C NMR (CDCl$_3$, 75 MHz): δ 146.4, 83.0, 37.0, 33.0, 32.7, 31.2, 25.1, 22.7, 14.4, 14.3 (the C-atom directly attached to boron is broadened and could not be precisely localized); $^{11}$B NMR (CDCl$_3$, 96 MHz): δ 30.6; HRMS (ESI): m/z calcd for C$_{16}$H$_{31}$BO$_2$Na [M$^+$+Na]: 289.2322. found: 289.2322.

EXAMPLE 4

(E)-3-(4,4,5,5-Tetramethyl-1,3,2-dioxaborolan-2-yl) hex-3-ene-1,6-diylbis(4-chlorobenzoate)

White solid (73 mg, 94%); reaction time=140 min, $^1$H NMR (CDCl$_3$, 300 MHz): δ 7.97-7.86 (4H, m), 7.40-7.29 (4H, m), 6.24 (1H, t, J=7.5 Hz), 4.40-4.26 (4H, m), 2.83 (2H, q, J=6.4, 13.6 Hz), 2.57 (2H, t, J=6.6 Hz), 1.24 (12H, 5), $^{13}$C NMR (CDCl$_3$, 75 MHz): δ 165.60, 165.55, 144.9, 139.2, 139.1, 130.9, 130.8, 129.0, 128.9, 128.53, 128.52, 83.2, 65.0, 64.8, 36.1, 30.6, 24.7 (the C-atom directly attached to boron is broadened and could not be precisely localized); $^{11}$B NMR (CDCl$_3$, 128 MHz): δ 30.7; HRMS (ESI): m/z calcd for C$_{26}$H$_{29}$BCl$_2$O$_6$Na [M$^+$+Na]: 541.1338. found: 541.1338.

EXAMPLE 5

(E)-3-(4,4,5,5-Tetramethyl-1,3,2-dioxaborolan-2-yl) hex-3-ene-1,6-diyl bis(4-methoxybenzoate)

Colorless oil (40 mg, 75%); reaction time=1 h; $^1$H NMR (CDCl$_3$, 400 MHz): δ=7.89 (2H, d, J=3.5 Hz), 7.87 (2H, d, J=3.5 Hz), 6.87 (2H, d, J=8.8 Hz), 6.84 (2H, d, J=8.8 Hz), 6.28 (1H, t, J=7.3 Hz), 4.36-4.25 (4H, m), 3.84 (3H, s), 3.82 (3H, s), 2.83 (2H, q, J=6.8, 13.6 Hz), 2.56 (2H, t, J=6.6 Hz), 1.24 (12H, 5), $^{13}$C NMR (CDCl$_3$, 75 MHz): δ 166.30, 166.25, 163.2, 163.1, 145.1, 131.54, 131.45, 123.1, 123.0, 113.47, 113.45, 83.2, 64.5, 64.4, 55.32, 55.31, 36.2, 30.8, 24.8 (the C-atom directly attached to boron is broadened and could not be precisely localized); $^{11}$B NMR (CDCl$_3$, 128 MHz): δ 29.7; HRMS (ESI): m/z calcd for C28H35BO$_8$Na [M$^+$+Na]: 533.2330. found: 533.2333.

EXAMPLE 6

(E)-29-Nitro-13-(4,4,5,5-tetramethyl-1,3,2-dioxaborolan-2-yl)-3,4,5,6,7,8,9,10,11,12,15,16,17,18,19,20,21,22,23,24-icosahydrobenzo[c][1,6]dioxacyclooctacosine-1,26-dione White solid (48 mg, 77%); reaction time=4 h; $^1$H NMR (CDCl$_3$, 400 MHz): δ 8.60 (1H, d, J=2.27 Hz), 8.37 (1H, 2d, J=2.2 Hz), 7.84 (1H, d, J=8.3 Hz), 5.93 (1H, t, J=7.4 Hz), 4.40-4.26 (4H, m), 2.33 (2H, q, J=6.5, 13.3 Hz), 2.09 (2H, t, J=6.3 Hz), 1.82-1.67 (4H, q, J=7.0, 14.1 Hz), 1.46-1.13 (40H, m); $^{13}$C NMR (CDCl$_3$, 125 MHz): δ 166.3, 165.2, 148.7, 147.1, 138.2, 133.2, 130.1, 125.8, 124.4, 82.6, 66.6, 36.2, 30.49, 30.47, 29.6, 29.5, 29.4, 29.32, 29.28, 29.2, 28.5, 28.43, 28.39, 28.37, 28.26, 28.21, 28.04, 27.96, 25.70, 25.65, 24.8 (the C-atom directly attached to boron is broadened and could not be precisely localized); $^{11}$B NMR (CDCl$_3$, 128 MHz): δ 31.0; HRMS (ESI): m/z calcd for C$_{36}$H$_{56}$BNO$_8$Na [M$^+$+Na]: 664.4007. found: 664.4009.

EXAMPLE 7

(E)-2-(1,6-Bis(benzyloxy)hex-3-en-3-yl)-4,4,5,5-tetramethyl-1,3,2-dioxaborolane Colorless oil, (65 mg, 83%); reaction time=2 h 30 min, $^1$H NMR (CDCl$_3$, 400 MHz): δ 7.34-7.12 (10H, m), 6.09 (1H, t, J=7.3 Hz), 4.44 (2H, s), 4.42 (2H, s), 3.41 (4H, q, J=7.0, 15.0 Hz), 2.61 (2H, q, J=7.10, 14.2 Hz), 2.36 (2H, t, J=7.1 Hz), 1.14 (12H, 5), $^{13}$C NMR (CDCl$_3$, 125 MHz): δ 144.3, 143.3, 138.8, 138.6, 128.3, 128.2, 127.6, 127.4, 127.3, 82.9, 72.6 (2C), 70.7, 70.2, 37.1, 31.6, 24.7 (the C-atom directly attached to boron is broadened and could not be precisely localized); $^{11}$B NMR (CDCl$_3$, 128 MHz): δ 30.9; HRMS (ESI): m/z calcd for C$_{26}$H$_{35}$BO$_4$Na [M$^+$+Na]: 445.2532. found: 445.2536.

EXAMPLE 8

(E)-3-(4,4,5,5-Tetramethyl-1,3,2-dioxaborolan-2-yl)hex-3-ene-1,6-diylbis(4-methylbenzene-sulfonate)

Colorless oil (40 mg, 73%); reaction time=2 h 30 min, $^1$H NMR (CDCl$_3$, 300 MHz): δ=7.82-7.72 (4H, m), 7.38-7.28 (4H, m), 5.92 (1H, t, J=7.3 Hz), 4.06-3.93 (4H, m), 2.68 (2H, q, J=6.8, 13.9 Hz), 2.44 (3H, s), 2.43 (3H, s), 2.35 (2H, t, J=6.8 Hz), 1.16 (12H, 5), $^{13}$C NMR (CDCl$_3$, 75 MHz): δ 144.6, 144.5, 144.0, 133.4, 133.2, 129.8, 129.7, 127.9 (2C), 83.3, 70.2, 70.0, 36.2, 30.5, 24.7, 21.56, 21.55 (the C-atom directly attached to boron is broadened and could not be precisely localized); HRMS (ESI): m/z calcd for C$_{26}$H$_{35}$BO$_8$Na [M$^+$+Na]: 573.1770. found: 573.1773.

EXAMPLE 9

(E)-2-(1,6-Bis((tetrahydro-2H-pyran-2-yl)oxy)hex-3-en-3-yl)-4,4,5,5-tetramethyl-1,3,2-dioxa borolane Colorless oil (42 mg, 61%); reaction time=2 h; $^1$H NMR (CDCl$_3$, 400 MHz): δ 6.16 (1H, t, J=7.5 Hz), 4.62-4.55 (2H, m), 3.92-3.80 (2H, m), 3.77-3.64 (2H, m), 3.52-3.35 (4H, m), 2.71-2.57 (2H, m), 2.39 (2H, t, J=7.4 Hz), 1.91-1.75 (2H, m), 1.74-1.62 (2H, m), 1.62-1.42 (8H, m), 1.24 (12H, 5), $^{13}$C NMR (CDCl$_3$, 125 MHz): δ 144.8, 98.4 (2C), 82.9, 67.7, 67.3, 62.1, 62.0, 37.0, 31.6, 30.7 (2C), 25.5 (2C), 24.8, 19.5 (2C) (the C-atom directly attached to boron is broadened and could not be precisely localized); $^{11}$B NMR (CDCl$_3$, 128 MHz): δ 30.7; HRMS (ESI): m/z calcd for C$_{26}$H$_{39}$BO$_6$Na [M$^+$+Na]: 433.2734. found: 433.2731.

EXAMPLE 10

(E)-3,3'-((13-(4,4,5,5-Tetramethyl-1,3,2-dioxaborolan-2-yl)hexacos-13-ene-1,26-diyl)bis(oxy))-dibenzonitrile White solid (53 mg, 87%); reaction time=4 h; $^1$H NMR (CDCl$_3$, 400 MHz): δ 7.47-7.30 (3H, m), 7.24-7.18 (2H, m), 7.12 (3H, m), 5.97 (1H, t, J=7.3 Hz), 3.95 (4H, t, J=6.5 Hz), 2.28 (2H, q, J=6.8 Hz), 2.13 (1H, t, J=6.0 Hz), 2.06 (2H, t, J=6.9 Hz), 1.85-1.73 (4H, m), 1.51-1.39 (6H, m), 1.39-1.20 (41H, m); $^{13}$C NMR (CDCl$_3$, 150 MHz): δ 159.1, 145.9, 135.2, 134.9, 130.2, 130.0, 127.9, 124.2, 119.8, 118.8, 117.3, 113.1, 82.9, 80.2, 68.4, 53.4, 36.9, 31.1, 30.3, 30.14, 30.04, 29.62, 29.60, 29.58, 29.56, 29.55, 29.51, 29.46, 29.29, 29.24, 29.14, 29.13, 29.0, 28.8, 28.5, 25.9, 24.8, 18.7 (the C-atom directly attached to boron is broadened and could not be precisely localized); $^{11}$B NMR (CDCl$_3$, 77 MHz): δ 31.0, HRMS (ESI): m/z calcd for C$_{46}$H$_{69}$BN$_2$O$_4$Na [M$^+$+Na]: 747.5264. found: 747.5261.

EXAMPLE 11

(E)-Di-tert-butyl(5-(4,4,5,5-tetramethyl-1,3,2-dioxaborolan-2-yl)dec-5-ene-1,10-diyl)bis(benzyl carbamate)

Colorless oil (87 mg, 82%); reaction time=23 h; $^1$H NMR (CDCl$_3$, 400 MHz): δ 7.28-7.08 (10H, m), 5.85 (1H, t, J=7.4 Hz), 4.43-4.25 (4H, m), 3.22-2.94 (4H, m), 2.20 (2H, q, J=7.3, 14.6 Hz), 1.97 (2H, t, J=7.3 Hz), 1.53-1.27 (22H, m), 1.26-1.16 (4H, m), 1.15 (12H, 5), $^{13}$C NMR (CDCl$_3$, 125 MHz): δ 155.8, 155.3, 145.7, 138.3, 132.5, 128.1 (3C), 127.3, 126.7, 115.1, 82.7, 79.1 (2C), 50.0, 49.6, 46.2, 36.3, 36.2, 30.4, 28.1, 27.1 (2C), 27.0, 24.44, 24.39, 24.2 (the C-atom directly attached to boron is broadened and could not be precisely localized); $^{11}$B NMR (CDCl$_3$, 96 MHz): δ 31.1; HRMS (ESI): m/z calcd for C$_{40}$H$_{61}$BN$_2$O$_6$Na [M$^+$+Na]: 699.4521. found: 699.4514.

EXAMPLE 12

(E)-N$^1$,N$^8$-Dimethoxy-N$^1$,N$^8$-dimethyl-4-(4,4,5,5-tetramethyl-1,3,2-dioxaborolan-2-yl)oct-4-ene-diamide Colorless oil (39 mg, 85%); reaction time=5 h; $^1$H NMR (CDCl$_3$, 300 MHz): δ 6.09 (1H, t, J=7.3 Hz), 3.65 (3H, s), 3.64 (3H, s), 3.15 (3H, s), 3.14 (3H, s), 2.61 (2H, q, J=7.2, 14.8 Hz), 2.54-2.31 (6H, m), 1.24 (12H, 5), $^{13}$C NMR (CDCl$_3$, 75 MHz): δ 174.4 (2C), 145.7, 83.0, 61.1 (2C), 32.7, 32.3, 32.2 (2C), 26.28, 26.25, 24.8 (the C-atom directly attached to boron is broadened and could not be precisely localized); $^{11}$B NMR (CDCl$_3$, 96 MHz): δ 29.6; HRMS (ESI): m/z calcd for C$_{18}$H$_{33}$BN$_2$O$_6$Na [M$^+$+Na]: 407.2331. found: 407.2337.

EXAMPLE 13

(E)-2-(1,12-Dibromododec-6-en-6-yl)-4,4,5,5-tetramethyl-1,3,2-dioxaborolane Colorless oil, (77 mg, 85%); reaction time=4 h; $^1$H NMR (CDCl$_3$, 400 MHz): δ 5.97 (1H, t, J=7.5 Hz), 3.39 (4H, t, J=6.9 Hz), 2.31 (2H, q, J=7.4, 14.5 Hz), 2.07 (2H, t, J=6.7 Hz), 1.92-1.78 (4H, m), 1.48-1.31 (8H, m), 1.26 (12H, 5), $^{13}$C NMR (CDCl$_3$, 125 MHz): δ 146.0, 82.8, 36.5, 34.0, 33.9, 32.7, 32.6, 30.7, 29.3, 28.9, 27.7, 27.5, 24.8 (the C-atom directly attached to boron is broadened and could not be precisely localized); $^{11}$B NMR (CDCl$_3$, 128 MHz): δ 31.1; HRMS (ESI): m/z calcd for C$_{18}$H$_{33}$BBr$_2$O$_2$Na [M$^+$+Na]: 473.0842. found: 473.0832.

EXAMPLE 14

(E)-9-(4,4,5,5-Tetramethyl-1,3,2-dioxaborolan-2-yl)-1,6-dioxacyclododec-9-ene-2,5-dione White solid (27 mg, 54%); reaction time=20 min, $^1$H NMR (CDCl$_3$, 400 MHz): δ 5.95 (1H, t, J=6.4 Hz), 4.36-4.21 (4H, m), 2.75 (2H, q, J=6.1, 13.0 Hz), 2.55 (4H, m), 2.40 (2H, t, J=5.6 Hz), 1.27 (12H, s); $^{13}$C NMR (CDCl$_3$, 75 MHz): δ 171.84, 171.83, 146.0, 83.0, 62.78, 62.76, 37.5, 30.6, 30.3, 30.2, 24.8 (the C-atom directly attached to boron is broadened and could not be precisely localized); $^{11}$B NMR (CDCl$_3$, 128 MHz): 30.4; HRMS (ESI): m/z calcd for C$_{16}$H$_{25}$B$_1$O$_6$Na [M$^+$+Na]: 347.1633. found: 347.1636.

EXAMPLE 15

1,1'-((E)-2-(4,4,5,5-Tetramethyl-1,3,2-dioxaborolan-2-yl)but-2-ene-1,4-diyl)bis(hexahydro-1H-inden-2(3H)-one)

Colorless oil (52 mg, 75%); reaction time=20 h; $^1$H NMR (CDCl$_3$, 400 MHz): δ 6.00 (1H, t, J=8.0 Hz), 2.74-2.61 (1H, m), 2.60-2.50 (2H, m), 2.30 (2H, ddd, J=6.5 Hz), 2.16-1.88 (6H, m), 1.87-1.70 (9H, m), 1.58-1.22 (6H, m), 1.18 (12H, s), 1.13-0.98 (4H, m); $^{13}$C NMR (CDCl$_3$, 125 MHz): δ 219.3, 219.2, 145.4, 82.9, 55.6, 55.5, 48.9, 48.5, 48.2, 44.9, 44.6, 41.7, 41.5, 35.51, 35.49, 31.43, 31.38, 30.7, 29.0, 26.3, 26.2, 26.1, 24.9 (the C-atom directly attached to boron is broadened and could not be precisely localized); $^{11}$B NMR (CDCl$_3$, 128 MHz): δ 30.6; HRMS (ESI): m/z calcd for C$_{28}$H$_{43}$BO$_4$Na [M$^+$+Na]: 477.3149. found: 477.3146.

EXAMPLE 16

(E)-2-(1,2-Di(thiophen-2-yl)vinyl)-4,4,5,5-tetramethyl-1,3,2-dioxaborolane The reaction was performed for 24 h at ambient temperature, after which an additional 5 mol % of the ruthenium catalyst was added and stirring was continued at 50° C. for 48 h; pale yellow oil (49 mg, 59%), $^1$H NMR (CDCl$_3$, 400 MHz): δ 7.61 (1H, s), 7.37 (1H, dd, J=1.2, 5.0 Hz), 7.21-7.18 (1H, m), 7.12-7.09 (1H, m), 7.09-7.05 (1H, m), 6.93-6.89 (2H, m), 1.30 (12H, 5), $^{13}$C NMR (CDCl$_3$, 125 MHz): δ 140.6, 139.2, 138.8, 131.5, 128.8, 127.4, 126.16, 126.15, 125.8, 83.9, 24.7 (the C-atom directly attached to boron is broadened and could not be precisely localized); $^{11}$B NMR (CDCl$_3$, 128 MHz): δ 31.3; HRMS (ESI): m/z calcd for C$_{16}$H$_{19}$BO$_2$S$_2$Na [M$^+$+Na]: 341.0815. found: 341.0811.

EXAMPLE 17

(E)-4,4,5,5-Tetramethyl-2-(oct-2-en-2-yl)-1,3,2-dioxaborolane

Colorless oil (163 mg, 68%); reaction time=3 h; spectroscopic data of the major isomer $^1$H NMR (CDCl$_3$, 400 MHz): δ 6.05 (1H, t, J=7.0 Hz), 2.29 (2H, q, J=6.9 Hz), 1.77-1.71 (2H, m), 1.42-1.15 (19H, m), 0.87 (3H, 5), $^{13}$C NMR (CDCl$_3$, 125 MHz): δ 147.4, 82.7, 31.4, 30.9, 29.6, 24.8, 22.5, 22.3, 14.0 (the C-atom directly attached to boron is broadened and could not be precisely localized); $^{11}$B NMR (CDCl$_3$, 128 MHz): δ 30.3; HRMS (ESI): m/z calcd for C$_{14}$H$_{27}$BO$_2$Na [M$^+$+Na]: 261.1999. found: 261.1996.

EXAMPLE 18

(E)-2-(4,4-Dimethylpent-2-en-2-yl)-4,4,5,5-tetramethyl-1,3,2-dioxaborolane Colorless oil (758 mg, 67%); reaction time=1 h; spectroscopic data of the major isomer $^1$H NMR (CDCl$_3$, 400 MHz): δ 6.27 (1H, d, J=1.6 Hz), 1.79 (3H, d, J=1.6 Hz), 1.24 (12H, s), 1.13 (9H, 5), $^{13}$C NMR (CDCl$_3$, 125 MHz): δ 155.0, 83.1, 34.2, 30.3, 24.8, 14.8 (the C-atom directly attached to boron is broadened and could not be precisely localized); $^{11}$B NMR (CDCl$_3$, 128 MHz): δ 31.1; HRMS (ESI): m/z calcd for C$_{13}$H$_{25}$BO$_2$Na [M$^+$+Na]: 247.1837. found: 247.1839.

EXAMPLE 19

(E)-7-(4,4,5,5-Tetramethyl-1,3,2-dioxaborolan-2-yl)oct-6-en-1-yl undec-10-enoate Colorless oil (49 mg, 60%); reaction time=3 h; spectroscopic data of the major isomer $^1$H NMR (CDCl$_3$, 300 MHz): δ 6.017 (1H, m), 5.78-5.72 (1H, m), 4.96-4.87 (2H, m), 4.02 (2H, m), 2.36-2.30 (2H, m), 2-30-2.25 (2H, m), 2.05-2.00 (2H, m), 1.72 (3H, s), 1.59-1.54 (4H, m), 1.33-1.26 (8H, m), 1.26-1.24 (6H, m), 1.25 (12H, s), $^{13}$C NMR (CDCl$_3$, 125 MHz): δ 174.0, 146.9, 139.2, 114.1, 82.8, 64.4, 30.7, 34.5, 33.8, 29.5, 29.3, 29.2, 29.1, 29.0, 28.9, 28.4, 25.3, 25.0, 24.8, 22.3 (the C-atom directly attached to boron is broadened and could not be precisely localized); $^{11}$B NMR (CDCl$_3$, 128 MHz): δ 30.1; HRMS (ESI): m/z calcd for C$_{25}$H$_{45}$BO$_4$Na [M$^+$+Na]: 443.3315. found: 443.3319.

EXAMPLE 20

(E)-2-(3-(4,4,5,5-Tetramethyl-1,3,2-dioxaborolan-2-yl)but-2-en-1-yl)isoindoline-1,3-dione Colorless oil (143 mg, 88%); reaction time=2 h; spectroscopic data of the major isomer $^1$H NMR (CDCl$_3$, 400 MHz): δ 7.87-7.74 (2H, m), 7.73-7.58 (2H, m), 5.97 (1H, t, J=6.4 Hz), 4.62 (2H, d, J=6.6 Hz), 1.75 (3H, s), 1.31 (12H, 5), $^{13}$C NMR (CDCl$_3$, 125 MHz): δ 168.0, 139.0, 133.7, 132.3, 123.0, 83.4, 38.4, 24.9, 16.9 (the C-atom directly attached to boron is broadened and could not be precisely localized); $^{11}$B NMR (CDCl$_3$, 128 MHz): δ 30.6; HRMS (ESI): m/z calcd for C$_{18}$H$_{22}$BO$_4$NNa [M$^+$]: 327.1641. found: 327.1641.

EXAMPLE 21 tert-Butyl (((1R,2S,E)-1-cyclohexyl-2-methyl-4-(4,4,5,5-tetramethyl-1,3,2-dioxaborolan-2-yl)pent-3-en-1-yl)oxy)dimethylsilane Colorless oil (106 mg, 70%); reaction time=2 h; spectroscopic data of the major isomer $^1$H NMR (CDCl$_3$, 400 MHz): δ 6.26 (1H, q, J=1.5, 3.2 Hz), 3.26-3.22 (1H, m), 2.79-2.68 (1H, m), 1.64 (3H, d, J=1.7 Hz), 1.22-1.20 (18H, m), 0.89-0.87 (14H, m), 0.85 (9H, s); $^{13}$C NMR (CDCl$_3$, 125 MHz): δ 150.4, 82.6, 80.4, 42.0, 36.8, 30.9, 28.6, 26.8, 26.6, 26.3, 25.0, 24.8, 22.7, 17.5, -3.3 (the C-atom directly attached to boron is broadened and could not be precisely localized); $^{11}$B NMR (CDCl$_3$, 128 MHz): δ 30.9; HRMS (ESI): m/z calcd for C$_{24}$H$_{47}$BO$_3$SiNa [M$^+$+Na]: 445.3276. found: 445.3279.

EXAMPLE 22

(E)-4,4,5,5-Tetramethyl-2-(1-(2-(methylthio)phenyl) prop-1-en-2-yl)-1,3,2-dioxaborolane Colorless oil, (54 mg, 91%), reaction time=160 min, spectroscopic data of the major isomer $^1$H NMR (CDCl$_3$, 400 MHz): δ 7.25 (1H, bs), 7.16-7.13 (2H, m), 7.13-7.11 (1H, m), 7.05-7.03 (1H, m), 2.35 (3H, s), 1.76 (3H, d, J=1.76 Hz), 1.23 (12H, 5), $^{13}$C NMR (CDCl$_3$, 125 MHz): δ 143.3, 139.2, 135.4, 128.4, 126.6, 124.2, 123.1, 82.4, 23.8, 14.8, 14.6 (the C-atom directly attached to boron is broadened and could not be precisely localized); $^{11}$B NMR (CDCl$_3$, 77 MHz): δ 31.1, HRMS (ESI): m/z calcd for C$_{16}$H$_{23}$BO$_2$SNa [M$^+$+Na]: 313.1404. found: 313.1404.

EXAMPLE 23

(E)-Methyl-4-(2-(4,4,5,5-tetramethyl-1,3,2-dioxaborolan-2-yl)prop-1-en-1-yl)benzoate Color-less oil, (106 mg, 70%); reaction time=3 h; spectroscopic data of the major isomer $^1$H NMR (CDCl$_3$, 400 MHz): δ 7.85-7.83 (2H, m), 7.30-7.26 (2H, m), 6.84 (1H, s), 3.81 (s, 3H), 1.92 (3H, d, J=1.7 Hz), 1.18 (12H, 5), $^{13}$C NMR (CDCl$_3$, 125 MHz): δ 166.95, 143.46, 139.69, 129.13, 127.87, 83.60, 24.58, 23.53 (the C-atom directly attached to boron is broadened and could not be precisely localized); spectroscopic data of the minor isomer $^1$HNMR (CDCl$_3$, 400 MHz): δ 7.88-7.86 (2H, m), 7.32-7.26 (2H, m), 6.48 (1H, q, J=7.0, 14.1 Hz), 3.80 (3H, s), 1.99 (3H, d, J=1.7 Hz), 1.24 (12H, 5), $^{13}$C NMR (CDCl$_3$, 125 MHz): δ 167.1, 148.2, 144.5, 129.4, 127.0, 83.5, 51.9, 24.7, 17.9 (the C-atom directly attached to boron is broadened and could not be precisely localized); $^{11}$B NMR (CDCl$_3$, 128 MHz): 31.5; HRMS (ESI): m/z calcd for C$_{17}$H$_{23}$BO$_4$Na [M$^+$+Na]: 325.1580. found: 325.1581.

EXAMPLE 24

(E)-4,4,5,5-Tetramethyl-2-(1-(4-(trifluoromethyl) phenyl)prop-1-en-2-yl)-1,3,2-dioxaborolane Yellow oil (100 mg, 64%); reaction time=80 min, spectroscopic data of the major isomer: $^1$H NMR (CDCl$_3$, 400 MHz): δ 7.57-7.50 (2H, m), 7.48-7.40 (2H, m), 6.94 (1H, s), 2.02 (3H, d, J=1.5 Hz), 1.27 (12H, s); $^{13}$C NMR (CDCl$_3$, 125 MHz): δ 142.1, 139.1, 128.0 (2C), 124.4 (q), 83.3, 24.3, 23.2 (the C-atom directly attached to boron is broadened and could not be precisely localized); spectroscopic data of the minor isomer $^1$H NMR (CDCl$_3$, 400 MHz): δ 7.56-7.50 (2H, m), 7.47-7.39 (2H, m), 6.56 (1H, q, J=7.0, 14.1 Hz), 2.11 (3H, d, J=7.0 Hz), 1.34 (12H, 5), $^{13}$C NMR (CDCl$_3$, 125 MHz): δ 146.9, 144.8, 127.1 (2C), 124.6 (q), 83.4, 24.5, 17.6; (the C-atom directly attached to boron is broadened and could not be precisely localized); $^{11}$B NMR (CDCl$_3$, 128 MHz): δ 29.7; HRMS (ESI): m/z calcd for C$_{16}$H$_{20}$BO$_2$F$_3$Na [M$^+$]: 312.1511. found: 312.1508.

EXAMPLE 25

(E)-11-Methyl-1,8-dioxacyclotetradec-11-ene-2,7-dione

Iodomethane (10.6 μL, 0.170 mmol) and KOH (24 mg, 0.426 mmol) were added to a solution of Pd(dba)$_2$ (4.08 mg, 0.007 mmol, 5 mol %), [HCy$_3$P]BF$_4$ (7.84 mg, 0.021 mmol, 15 mol %) and alkenyl boronate E-2 (50 mg, 0.142 mmol) in THF (1 mL) under argon. After stirring for 12 h at ambient temperature, the mixture was poured into diethyl ether (20 mL) before it was filtered through a pad of silica, which was carefully rinsed with diethyl ether (3×5 mL). Evaporation of the combined filtrates followed by flash chromatography (EtOAc/Hex, 4:1) gave the title compound as a colorless oil (18 mg, 53%). $^1$H NMR (CDCl$_3$, 400 MHz): δ 5.20 (1H, t, J=7.0, 14.1 Hz), 4.20 (2H, t, J=5.4 Hz), 4.13 (2H, t, J=5.5 Hz), 2.44-2.25 (8H, m), 1.64 (3H, s), 1.63 (4H, m); $^{13}$C NMR (CDCl$_3$, 125 MHz): δ 173.3, 173.1, 132.2, 123.7, 64.0, 60.9, 38.5, 35.0, 34.9, 27.2, 24.8, 24.6, 15.2; HRMS (ESI): m/z calcd for C$_{13}$H$_{20}$O$_4$Na [M$^+$+Na]: 263.1251. found: 263.1253.

EXAMPLE 26

(E)-1,8-Dioxacyclotetradec-11-ene-2,7-dione

AgF (21.6 mg, 0.170 mmol) was added to a solution of E-2 (30 mg, 0.08 mmol) in THF/MeOH/H$_2$O (10:9:1) (1 mL) under argon and the resulting mixture was stirred for 3 h in the dark. Insoluble materials were filtered off and carefully washed with Et$_2$O and EtOAc (3 mL each), the combined filtrates were evaporated and the residue was purified by flash chromatography (hexane/EtOAc, 4:1) to give the title compound as a colorless oil (15 mg, 78%; E/Z=98:2). $^1$H NMR (CDCl$_3$, 400 MHz): δ 5.47-5.43 (2H, m), 4.18-4.09 (4H, m), 2.44-2.24 (8H, m), 1.69-1.57 (4H, m); $^{13}$O NMR (CDCl$_3$, 125 MHz): δ 173.2, 129.2, 63.1, 35.0, 31.9, 24.7; HRMS (ESI): m/z calcd for C$_{12}$H$_{18}$O$_4$Na [M$^+$+Na]: 249.1095. found: 249.1097.

The invention claimed is:
1. Process for highly stereoselective trans-hydroboration of internal alkynes comprising the steps of reacting an alkyne of the formula I:

with a borane of the formula X$^1$X$^2$BH in the presence of a ruthenium catalyst to yield an alkene of the general formula (II):

wherein:
R$^1$ and R$^2$ are the same or different and are each be selected from:
 a. straight chain or branched chain aliphatic hydrocarbons, said aliphatic hydrocarbons optionally including heteroatoms and/or aromatic hydrocarbons and/or heteroaromatic hydrocarbons in the chain and/or having one or more substituents selected from C$_1$-C$_{20}$-alkyl, C$_5$-C$_8$-heterocycloalkyl or C$_6$ to C$_{20}$ aromatic hydrocarbon, C$_5$ to C$_{20}$ heteroaromatic hydrocarbon or aryl-(C$_1$-C$_6$)-alkyl, heteroaryl-(C$_1$-C$_6$)-alkyl, or heteroatoms, or
 b. aromatic hydrocarbons having 5 to 20 carbon atoms or heteroaromatic hydrocarbons having 1 to 20 carbon atoms, said aromatic or heteroaromatic hydrocarbons each optionally having one or more substituents selected from C$_1$-C$_{20}$-alkyl, C$_5$-C$_8$-heterocycloalkyl or C$_6$ to C$_{20}$ aromatic hydrocarbon, C$_5$ to C$_{20}$ heteroaromatic hydrocarbon or aryl-(C$_1$-C$_6$)-alkyl, heteroaryl-(C$_1$-C$_6$)-alkyl, heteroatoms, or
R$^1$ and R$^2$ together form an aliphatic hydrocarbon chain having 4 to 30 carbon atoms, optionally including heteroatoms and/or aromatic hydrocarbons in the chain and/or optionally having one or more substituents selected from C$_1$-C$_{20}$-alkyl, C$_5$-C$_8$-heterocycloalkyl or C$_6$ to C$_{20}$ aromatic hydrocarbon, C$_5$ to C$_{20}$ heteroaromatic hydrocarbon or aryl-(C$_1$-C$_6$)-alkyl, heteroaryl-(C$_1$-C$_6$)-alkyl, said aliphatic hydrocarbon chain optionally being substituted by one or more substituents selected from heterosubstituents, straight chain, branched chain, cyclic aliphatic C$_1$ to C$_{20}$ hydrocarbons, C$_6$ to C$_{20}$ aromatic hydrocarbon, C$_5$ to C$_{20}$ heteroaromatic hydrocarbon, aryl-(C$_1$-C$_6$)-alkyl, or heteroaryl-(C$_1$-C$_6$)-alkyl or heteroatoms;
wherein the borane of the formula X$^1$X$^2$BH is selected from the group of dialkyl boranes or di(alkoxy)boranes wherein X$^1$ and X$^2$ are the same or different and are each selected from straight chain, branched chain or cyclic aliphatic hydrocarbons, or X$^1$ and X$^2$ together form an aliphatic hydrocarbon chain having 2 to 20 carbon atoms, said aliphatic hydrocarbon—group or chain—optionally bound to the boron via an —O-bridge and optionally including heteroatoms in the chain and/or optionally having one or more substituents selected from C$_1$-C$_{20}$-alkyl, C$_5$-C$_8$-heterocycloalkyl or C$_6$ to C$_{20}$ aromatic hydrocarbon, C$_1$ to C$_{20}$ heteroaromatic hydrocarbon or aryl-(C$_1$-C$_6$)-alkyl, heteroaryl-(C$_1$-C$_6$)-alkyl, having identical or different alkyl groups with 2 to 12 carbon atoms or heteroatoms; and
wherein the catalyst used in the inventive process is a cyclyopentadienyl-coordinated ruthenium complex containing the following substructure:

wherein R$_{cp1}$ to R$_{cp5}$ are the same or different and are each selected from hydrogen or from straight chain, branched chain or cyclic aliphatic hydrocarbons, optionally including heteroatoms and/or aromatic hydrocarbons in the chain and/or optionally having one or more substituents selected from C$_1$-C$_{20}$-alkyl, heterocycloalkyl, C$_5$ to C$_{20}$ aromatic hydrocarbon, C$_5$ to C$_{20}$ heteroaromatic hydrocarbon or aryl-(C$_1$-C$_6$)-alkyl, heteroaryl-(C$_1$-C$_6$)-alkyl or heteroatoms and wherein further ligands L are coordinated to the central atom ruthenium.

2. Process for highly stereoselective trans-hydroboration of internal alkynes according to claim 1 wherein, in formulas (I) and (II):
R$^1$ and R$^2$ are the same or different and are each selected from straight chain or branched chain aliphatic hydrocarbons having 1 to 20 carbon atoms optionally including heteroatoms and/or aromatic hydrocarbons in the chain or aromatic hydrocarbons having 5 to 20 carbon atoms, optionally having one or more substituents selected from $C_1$-$C_{20}$-alkyl, $C_5$-$C_8$-heterocycloalkyl or $C_6$ to $C_{20}$ aromatic hydrocarbon, $C_5$ to $C_{20}$ heteroaromatic hydrocarbon or aryl-($C_1$-$C_6$)-alkyl, heteroaryl-($C_1$-$C_6$)-alkyl, or heteroatoms, or $R^1$ and $R^2$ together form an aliphatic hydrocarbon chain structure having 8 to 20 carbon atoms, optionally including heteroatoms and/or aromatic hydrocarbons in the chain and/or optionally having one or more substituents selected from $C_1$-$C_{20}$-alkyl, $C_5$-$C_8$-heterocycloalkyl or $C_6$ to $C_{20}$ aromatic hydrocarbon, $C_5$ to $C_{20}$ heteroaromatic hydrocarbon or aryl-($C_1$-$C_6$)-alkyl, heteroaryl-($C_1$-$C_6$)-alkyl, said chain structure optionally being substituted by one or more substituents selected from heterosubstituents, straight chain, branched chain, cyclic aliphatic $C_1$ to $C_{20}$ hydrocarbons, $C_6$ to $C_{20}$ aromatic hydrocarbon, $C_5$ to $C_{20}$ heteroaromatic hydrocarbon, aryl-($C_1$-$C_6$)-alkyl, or heteroaryl-($C_1$-$C_6$)-alkyl.

3. Process for highly stereoselective trans-hydroboration of internal alkynes according to claim 1, wherein, in the formula $X^1X^2BH$, $X^1$ and $X^2$ are each bound to the boron atom via an —O—bridge and form a hydrocarbon ring having 2 to 12 carbon atoms, said hydrocarbon ring optionally being substituted by one or more substituents selected from heterosubstituents, $C_1$ to $C_6$ straight chain, branched chain or cyclic aliphatic hydrocarbons, as represented by the general formula (III):

(III)

4. Process for highly stereoselective trans-hydroboration of internal alkynes according to claim 3 wherein, in the formula $X^1X^2BH$, $X^1$ and $X^2$ are each bound to the boron atom via an —O—bridge and form a hydrocarbon ring having 2 to 12 carbon atoms, said hydrocarbon ring, optionally being substituted by one or more substituents selected from hydrogen, methyl, ethyl, propyl, butyl or isomers thereof.

5. Process for highly stereoselective trans-hydroboration of internal alkynes according to claim 1, wherein pinacolborane (pin-H, 4,4,5,5-tetramethyl-1,3,2-dioxaborolane) is used as boran of the formula $X^1X^2BH$:

6. Process for highly stereoselective trans-hydroboration of internal alkynes according to claim 1, wherein 4,4,6-trimethyl-1,3,2-dioxaborinane is used as borane of the formula $X^1X^2BH$:

7. Process for highly stereoselective trans-hydroboration of internal alkynes according to claim 1, wherein the catalyst is [Cp*RuL$_3$]X wherein Cp*=$\eta^5$-$C_5R_{5cp}$ with each $R_{cp}$ being H or lower alkyl, and L being the same or different ligand/substituent and being selected from electron-donating ligands/substituents, and X is an anionic counter ion.

8. Process for highly stereoselective trans-hydroboration of internal alkynes according to claim 1, wherein the following complex is used as catalyst:

wherein the substituent R is selected from R=H, Me and $X^\ominus$ is an anionic counter ion.

9. Process for highly stereoselective trans-hydroboration of internal alkynes according to claim 7, wherein the anionic counterion is selected from $PF_6^-$, $SbF_6^-$, $BF_4^-$, $ClO_4^-$, $F_3CCOO^-$, $Tf_2N^-$, (Tf=trifluoromethanesulfonyl), $TfO^-$, tosyl, $[B[3,5-(CF_3)_2C_6H_3]_4]^-$, $B(C_6F_5)_4^-$ or $Al(OC(CF_3)_3)_4^-$.

10. Process for highly stereoselective trans-hydroboration of internal alkynes according to claim 1, wherein the catalyst is selected from the following complexes:

wherein the substituent X is selected from Cl, Br, I.

11. Method of using a ruthenium catalyst comprising a cyclyopentadienyl-coordinated ruthenium complex containing the following substructure:

wherein $R_{cp1}$ to $R_{cp5}$ are the same or different and are each selected from hydrogen or from straight chain, branched chain or cyclic aliphatic hydrocarbons, optionally including heteroatoms and/or aromatic hydrocarbons in the chain and/or optionally having one or more substituents selected from $C_1$-$C_{20}$-alkyl, heterocycloalkyl, $C_5$ to $C_{20}$ aromatic hydrocarbon, $C_5$ to $C_{20}$ heteroaromatic hydrocarbon or aryl-($C_1$-$C_6$)-alkyl, heteroaryl-($C_1$-$C_6$)-alkyl or heteroatoms and wherein further ligands L are coordinated to the central atom ruthenium, in a hydroboration reaction in the presence of an organic boron compound.

* * * * *

UNITED STATES PATENT AND TRADEMARK OFFICE
CERTIFICATE OF CORRECTION

PATENT NO. : 9,802,965 B2
APPLICATION NO. : 15/026374
DATED : October 31, 2017
INVENTOR(S) : Alois Fürstner et al.

It is certified that error appears in the above-identified patent and that said Letters Patent is hereby corrected as shown below:

In the Specification

Column 10, Line 1, "($\eta q^6$-arene)" -- should read -- ($\eta^6$-arene) --.

Column 11, Line 8, "7-complex" -- should read -- π-complex --.

Column 12, Line 13, "Tr-face" -- should read -- π-face --.

Column 13, Line 35, "(12H, 5)" -- should read -- (12H, s) --.

Column 14, Line 17, "(12H, 5)" -- should read -- (12H, s) --.

Column 14, Line 43, "(12H, 5)" -- should read -- (12H, s) --.

Column 14, Line 48, "C28H35" -- should read -- $C_{28}H_{35}$ --.

Column 15, Line 62, "(12H, 5)" -- should read -- (12H, s) --.

Column 16, Lines 19-20, "(12H, 5)" -- should read -- (12H, s) --.

Column 17, Line 5, "(12H, 5)" -- should read -- (12H, s) --.

Column 17, Line 60, "(12H, 5)" -- should read -- (12H, s) --.

Column 19, Line 26, "(12H, 5)" -- should read -- (12H, s) --.

Column 19, Line 49, "(9H, 5)" should read -- (9H, s) --.

Column 20, Lines 35-36, "(12H, 5)" -- should read -- (12H, s) --.

Signed and Sealed this
Second Day of July, 2019

Andrei Iancu
*Director of the United States Patent and Trademark Office*

Column 21, Line 26, "(12H, 5) -- should read -- (12H, s) --.

Column 21, Line 53, "(12H, 5)" -- should read -- (12H, s) --.

Column 22, Line 25, "(12H, 5)" -- should read -- (12H, s) --.

Column 23, Line 26, "$^{13}$O" -- should read -- $^{13}$C --.

In the Claims

Column 26, Line 26, Claim 9 "(CF$_3$)$_3$)$_4$" -- should read -- (CF$_3$)$_3$)$_4^-$ --.